United States Patent
Yan et al.

(10) Patent No.: US 8,730,460 B2
(45) Date of Patent: May 20, 2014

(54) PAPER BASED SPECTROPHOTOMETRIC DETECTION OF BLOOD HEMOGLOBIN CONCENTRATION

(75) Inventors: Jasper S. Yan, Houston, TX (US); Meaghan McNeill Bond, Houston, TX (US); John Neil Wright, Tiki Island, TX (US); Carlos Elguea, Dallas, TX (US); Rebecca Rae Richards-Kortum, Houston, TX (US)

(73) Assignee: William Marsh Rice University, Houston, TX (US)

( * ) Notice: Subject to any disclaimer, the term of this patent is extended or adjusted under 35 U.S.C. 154(b) by 40 days.

(21) Appl. No.: 13/441,452

(22) Filed: Apr. 6, 2012

(65) Prior Publication Data

US 2012/0257188 A1 Oct. 11, 2012

Related U.S. Application Data

(60) Provisional application No. 61/473,641, filed on Apr. 8, 2011.

(51) Int. Cl.
*G01N 33/48* (2006.01)

(52) U.S. Cl.
USPC .............................. 356/40; 356/39

(58) Field of Classification Search
USPC ...................... 356/39–42, 335–343, 432–436, 356/441–442, 72; 600/320, 321, 310, 316, 600/322, 323, 328, 339, 473, 476, 475, 160, 600/407, 477, 478, 182; 359/1, 3, 10, 15; 250/339.12, 341.1, 343
See application file for complete search history.

(56) References Cited

U.S. PATENT DOCUMENTS

| | | | | |
|---|---|---|---|---|
| 4,454,229 | A * | 6/1984 | Zander et al. | 436/68 |
| 5,316,727 | A * | 5/1994 | Suzuki et al. | 422/68.1 |
| 5,477,051 | A * | 12/1995 | Tsuchiya | 250/341.1 |
| 2003/0123047 | A1* | 7/2003 | Pettersson et al. | 356/39 |
| 2006/0203226 | A1* | 9/2006 | Roche et al. | 356/39 |

* cited by examiner

*Primary Examiner* — Tri T Ton
(74) *Attorney, Agent, or Firm* — Fletcher Yoder, P.C.

(57) ABSTRACT

The present disclosure relates to the use of a paper medium to measure blood hemoglobin concentration. In certain embodiments, spectrophotometric techniques are used to measure light transmission at specified wavelengths through a paper medium containing a blood sample. The light transmission information is then used in the calculation of blood hemoglobin concentration. In certain embodiments, the paper medium may be chemically treated to lyse the blood sample prior to measurement of the light transmission information.

9 Claims, 7 Drawing Sheets

US 8,730,460 B2

PAPER BASED SPECTROPHOTOMETRIC DETECTION OF BLOOD HEMOGLOBIN CONCENTRATION

CROSS-REFERENCE TO RELATED APPLICATIONS

This application claims the benefit of U.S. Provisional Patent Application No. 61/473,641, entitled "Filter Paper Based Spectrophotometric Detection of Blood Hemoglobin Concentration," and filed Apr. 8, 2011, which is herein incorporated by reference in its entirety for all purposes.

BACKGROUND

The present disclosure relates generally to the measurement of physiological properties, such as hemoglobin concentration, using a paper medium in conjunction with spectrophotometry.

Anemia is a major global health problem that affects a quarter of the world's population. Anemia can be caused by iron deficiency, blood loss, parasite infections (e.g. malaria), and acute and chronic infections (e.g. tuberculosis, HIV), among others. Anemia is diagnosed by measuring the concentration of hemoglobin in the blood. Once the condition is diagnosed, the underlying cause can be determined and treated with, for example, iron supplements for iron deficiency, anti-malarial drugs for malaria infection, or blood transfusion.

Hemoglobin concentration assessment is one of the most commonly performed laboratory tests worldwide and therefore serves as an important component of any healthcare system. Measurement systems that employ cuvettes are standard for hemoglobin assessment, but the cost of each single-use cuvette prevents widespread utilization, especially in low-resource rural areas, where anemia prevalence is high. Thus, there is a need for a low-cost alternative to conventional cuvette-based measurement systems.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Hemoglobin assessment is a commonly performed laboratory test and is essential to any healthcare system. Measurement systems that employ cuvettes are standard for hemoglobin assessment, but the cost of each single-use cuvette prevents widespread utilization. As discussed herein, paper (e.g., filter paper, chromatography paper, and so forth) can serve as a low-cost medium for accurate spectrophotometric detection of blood hemoglobin concentration. Such a paper based approach may offer benefits in terms of cost and availability or suitability in certain environments. The ability to accurately measure hemoglobin while reducing cost and reducing biohazard risk represents an important development in increasing accessibility of this important and basic clinical metric to developing countries.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF SPECIFIC EMBODIMENTS

Figure 1:
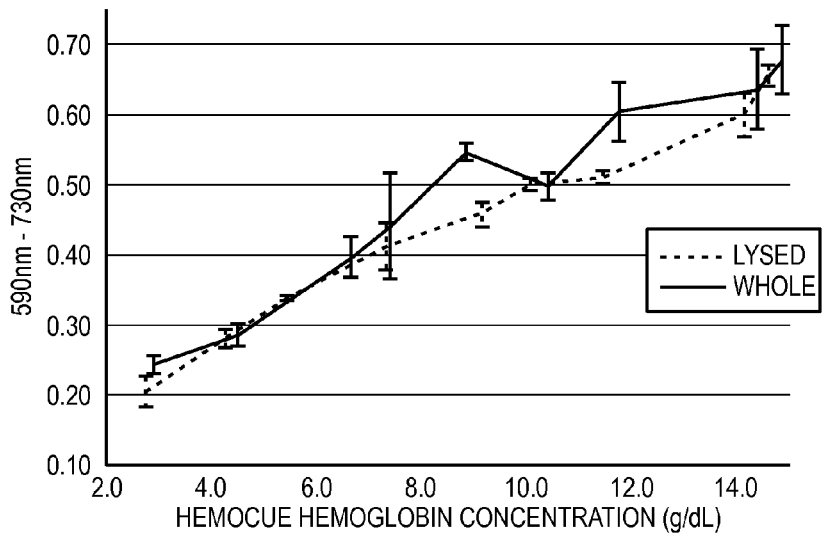
FIG. 1 depicts the difference in absorbance at two wavelengths for whole and lysed blood, in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, the calculations, correlations, and/or measurements discussed herein may be performed using one or more suitable computer-implemented algorithms, such as may be stored on a computer-readable memory or medium for execution by a suitable processing component in communication with the medium or memory. In addition, previously determined constants or correlations may be stored on the computer-readable memory or medium and accessed by the processing component during execution of the algorithms. The processor may also receive inputs or measurements from a measurement device, such as a spectrophotometer, or from personnel. Such inputs may be processed and/or used as inputs to the algorithms during execution of the algorithms. Examples of devices having suitable processing components, memory components, user interface circuitry, and/or circuitry for accessing local or remote media include, but are not limited to, desktop, notebook, and tablet computers, personal digital assistants, cellular telephones, media players, and so forth.

The ubiquitous and low-cost nature of filter paper (and other paper mediums) represents an attractive alternative to expensive, plastic cuvettes used in current spectrophotometric detection of blood hemoglobin concentration in systems, such as HemoCue®. The present disclosure demonstrates that paper can serve as a low-cost medium for accurate spectrophotometric detection of blood hemoglobin concentration. Experimental results indicate that average difference in absorbance between the respective target wavelengths are well-correlated to hemoglobin concentration determined using conventional techniques.

MATERIALS AND METHODS: Blood Samples, Paper Medium and Blood/Plasma Delivery. Informed consent was obtained from all human adult volunteers, and this project was approved by the Rice University Institutional Review Board (IRB). Blood samples for certain experiments were obtained by venous blood draw from healthy adult volunteers and stored for a maximum of 48 hours at 4° C. in heparinized tubes. In experiments where blood was applied to detergent-treated paper, samples were occasionally stored for longer periods. To simulate anemia, dilutions of whole blood were prepared using purified plasma (Gulf Coast Regional Blood Center, Houston, Tex.). Blood samples for the normal volunteer study were obtained via pinprick from healthy adult subjects.

In certain experiments, Whatman Grade 40 quantitative filter paper (Whatman, Piscataway, N.J.) was obtained and cut to dimensions of 1.75 in (i.e., 4.445 cm) by 0.5 in (i.e., 1.27 cm), and all blood and plasma samples were delivered via micropipette to the filter paper. In certain experiments, the blood spot formed on the filter paper was about 3 mm in diameter or greater.

In further experiments, chromatography paper having dimensions of 3.5 cm×1.5 cm and a thickness of 210 µm was used. In these experiments, 10 µL of 4% (w/v) sodium deoxycholate (SDOC) in phosphate buffered saline (PBS) was dried onto the paper medium. The paper medium employed was Whatman Grade 4 Chr4 (Whatman, Piscataway, N.J.), which was found to allow the blood to spread quickly and easily over the paper. After the detergent was dried, 10 µL of whole blood was spotted onto the paper via micropipette and allowed to dry for two minutes (except in those experiments where drying time was varied to analyze the effects of drying time). The chromatography paper was then placed in a spectrophotometer for analysis. Measurements from the resulting spectrum were correlated with hemoglobin concentrations of the same blood sample obtained from a HemoCue®.

Further, it is envisioned that in certain embodiments a target, such as a printed circle, may be pre-printed on the paper medium to help a health care provider control the volume of blood placed on the paper. For example, in such an embodiment a circle having a diameter of approximately 8 mm may be printed on the paper medium such that a blood sample that generally fills the printed circle corresponds to an approximate volume of blood in the range of about 10 µl to 15 µl. In such an embodiment, the health care provider may be instructed to prick the patient's finger and fill the printed circle with blood prior to spectrophotometric analysis of the blood sample.

Spectrophotometric Readings. All spectrophotometric readings discussed herein were taken using a Cary 5000 UV-Vis-NIR spectrophotometer (Varian, Palo Alto, Calif.). In other implementations, a low-cost and/or portable reader may be employed that uses LEDs configured to emit light at the appropriate frequency or frequencies, as discussed herein (such as at the 590 nm isosbestic point). In such low-cost or portable embodiments, the processing component may be a suitable low-cost or low-power consumption component, such as a processing component suitable for use in a cellular-telephone or other similar portable electronic device.

With the foregoing in mind, in a first set of experiments, optical densities of blood samples on filter paper were measured at wavelengths of 400 nm to 800 nm with a data interval of 1 nm at a sampling rate of 600 nm/minute. Filter paper samples were placed for spectrophotometric readings in a solid sample holder with 1 mm aperture masks for both reference and test filter paper samples.

In other experiments, optical densities of blood samples on paper media were measured at wavelengths of 400 nm to 750 nm with a data interval of 2 nm at a sampling rate of 600 nm/minute. Solid sample apertures with square 3 mm×3 mm apertures were used for both sample and reference beams. The reference beam contained only an aperture for all experiments.

Red Blood Cell Lysis. In certain implementations discussed herein, the red bloods cells are lysed prior to spectroscopic analysis. For example, in one experiment, to achieve mechanical lysis whole blood was taken through multiple (i.e., ≥3) freeze-thaw cycles (−20° C. to 20° C.). If high centrifugation did not separate the blood into plasma and cell layers and microscopy showed no intact cells, the blood was considered lysed.

In other implementations, chemical lysis of the blood cells is performed on the paper medium. For example, in one such implementation, a detergent, such as sodium deoxycholate, is used to chemically lyse the blood cells on the paper medium.

By way of example, in one set of experiments to optimize the volume and concentration of sodium deoxycholate, blood samples were examined in solution. In solution, lysed blood has a lower baseline because of the decreased turbidity compared to whole blood and much higher peaks than whole blood, presumably due to the pigment packaging effect. In these experiments, paper strips were treated with 2% or 4% (w/v) sodium deoxycholate in PBS at volumes of 10 µL to 50 µL in 10 µL increments. Volumes were added in coats of 10 µL at a time so that the sodium deoxycholate did not spread beyond the region where 10 µL of blood would spread. After drying, 10 µL whole blood was applied to the treated paper. Mechanically lysed blood was applied to untreated paper as a control. The blood dried for 2 minutes and the blood eluted from the paper in 1 mL PBS for 10 minutes. The paper was removed and spectra of the remaining solution were taken. 10 µL of 4% sodium deoxycholate was chosen for all further experiments because its spectrum closely matched that of mechanically lysed blood (which generated repeatable results), the blood spread quickly and evenly on the paper, and manufacturing the strips only required one drying step for the sodium deoxycholate solution.

Choice of Wavelength and Time. To determine the effects of drying time, absorption spectra of whole blood spotted on sodium deoxycholate-treated paper were analyzed over the course of 30 minutes, the time period during which a blood hemoglobin concentration assessment can be realistically performed in the field. In certain experiments, initial baseline correction was performed on the paper medium with freshly delivered plasma. Ten microliter whole blood and plasma (reference) samples were delivered via micropipette to two separate filter papers (or other paper media) to simulate blood volume drawn via finger prick. Spectrophotometric readings were taken every two minutes for a total duration of 30 minutes. Analysis was performed on this data to determine suitable pairs of wavelengths that would yield consistent hemoglobin measurements even if the drying time of the blood spot was varied.

Spectrophotometric Detection of Simulated Anemia on Paper Media. In initial experiments, spectrophotometric readings (n=2) of healthy to severely anemic concentrations of blood (100% to 10% respectively, in 10% gradations) were taken and analyzed at bandwidths centered around 577 nm and around 680 nm. It should appreciated that the choice of wavelengths may be approximate and that other wavelengths may be employed for one or both of these wavelengths (such as 590 nm in place of 577 nm, as discussed herein). For example, in one implementation the sample may be illuminated with two narrow-band light sources with center wavelengths near the specified region (e.g., at 577 nm or 590 nm and at 680 nm) and with bandwidths between about 5 nm to about 25 nm.

HemoCue® Hb 201+ (HemoCue, Ängelholm, Sweden) was used to measure clinical hemoglobin concentration for each blood concentration. Blood and plasma samples were delivered via micropipette to the filter paper at a volume of 10 µL. For consistent drying time, all blood samples were allowed to sit for 10 minutes before spectrophotometric measurement. The difference between optical densities at 577 nm and 680 nm were plotted against clinical, hemoglobin concentrations, and linear and power regression analyses were used to determine coefficient of determination ($r^2$) between optical density and hemoglobin concentration.

By subtracting the optical densities at the wavelengths of interest, baseline issues inherent in the spectrophotometric reading of blood on a paper medium are accounted for. That is, measuring the difference between optical densities at 2 wavelengths of the absorbance spectrum of blood rather than the measurement of one optical density at one wavelength corrects for the baseline issues observed by the negative optical densities as seen above 650 nm. Minimization of baseline issues leads to an increased $r^2$ correlation value for the linear and power regression models, and therefore more accurate hemoglobin measurement.

Volume Effects. To determine the effects of volume and spread, absorption spectra of various volumes (e.g., 5 µL, 10 µL, 15 µL, 20 µL) of whole blood on were obtained and analyzed. In certain experiments, initial baseline correction was performed on blank filter paper, and two readings were taken for each volume. HemoCue® Hb 201+ was used to determine the hemoglobin concentration for this whole blood sample. Differences between average values of optical density at 577 nm and 680 nm were determined, and percent error was calculated by comparing the HemoCue® hemoglobin values against values obtained from previously established power correlations.

In other experiments, three readings were taken for each volume. Differences between average values of optical density at 590 nm and at 730 nm were determined and plotted against blood volume.

TRAINING AND VALIDATION. Blood samples were used to train and validate the present approach. In one set of experiments, 43 patient samples of whole blood from venous draws were obtained. Additional samples were obtained for normal volunteers via fingerprick. Patient samples were discarded if the blood showed significant clotting. Approximately one-half of the hospital samples were used to train the system by correlating the samples' hemoglobin concentrations given by the HemoCue® with the absorbance difference between 590 nm and 730 nm using a best-fit power curve. The remaining one half of the hospital samples were tested with both the HemoCue® and the spectrometer to validate the correlation obtained with the training set.

Figure 2:
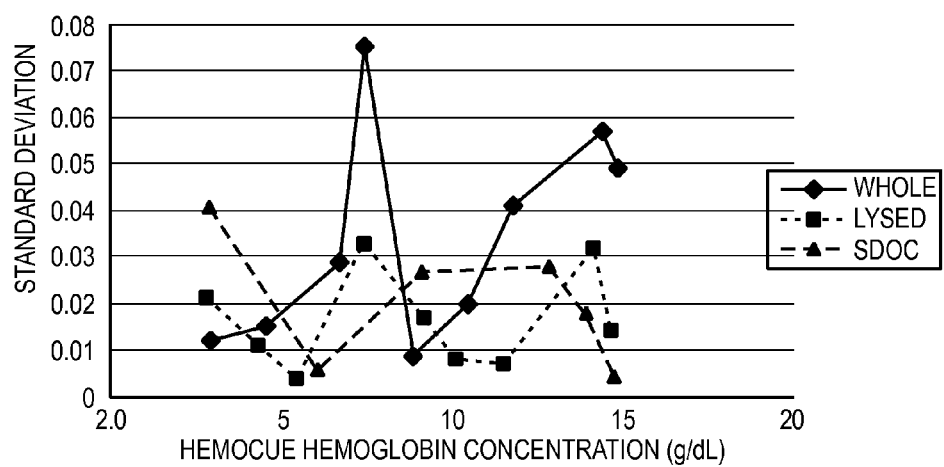
FIG. 2 depicts standard deviations of repeated measurements of the absorbance difference in FIG. 1 for whole and lysed blood, in accordance with aspects of the present disclosure.
Figure 3:
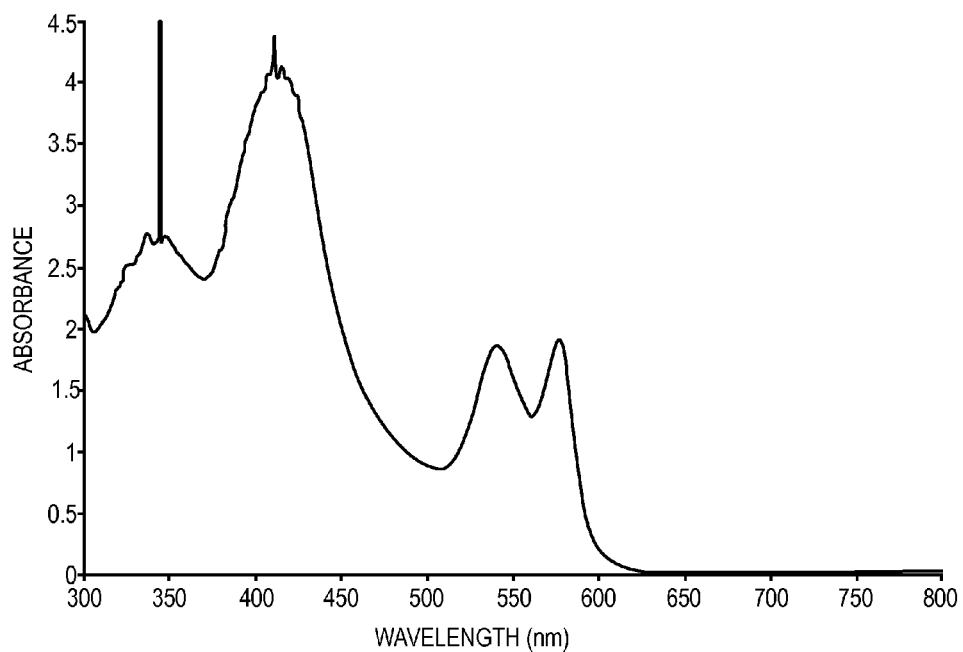
FIG. 3 depicts absorption spectra of 10 µL whole blood on Whatman 40 filter paper after 10 minutes of drying, adjusted so that the absorbance at 700 nm is zero, in accordance with aspects of the present disclosure.
Figure 4:
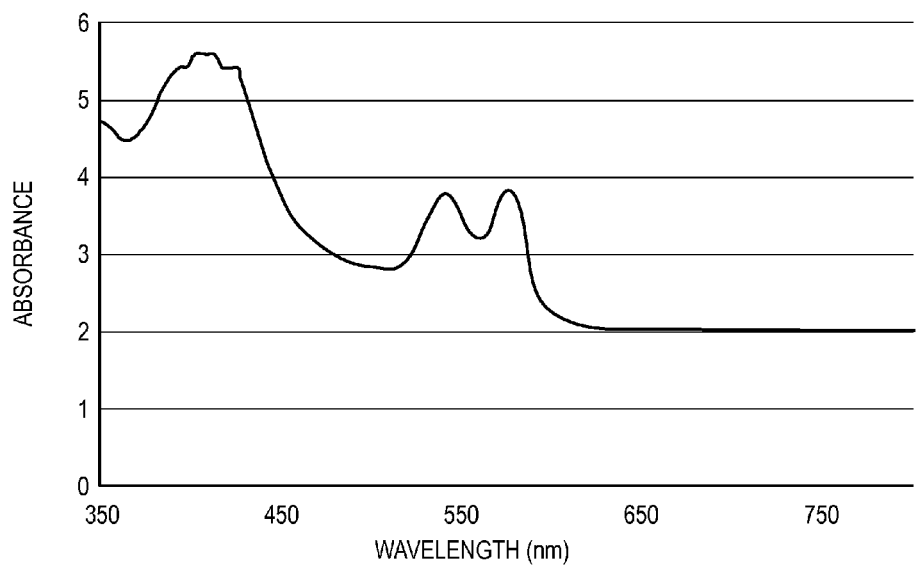
FIG. 4 depicts the unadjusted absorption spectra of blood on filter paper treated with a detergent, in accordance with aspects of the present disclosure.

Results and Discussion:

Lysed blood gives more repeatable results than whole blood. Turning to the figures, FIGS. 1 and 2 depicts experimental results comparing lysed and whole blood. With respect to FIG. 1, all blood samples were taken from one venous draw of a healthy volunteer. Half of the blood was mechanically lysed using freeze-thaw cycles. All blood was spotted on untreated paper. Lysed and whole blood was diluted with purchased plasma to simulate anemia. Error bars represent the standard deviation of three trials. While the error bars for lysed and whole blood are similar at low (<7 g/dL) hemoglobin concentrations, lysed blood has smaller error bars at high hemoglobin concentrations. With respect to FIG. 2, standard deviations are graphed for mechanically lysed and whole blood on untreated paper and whole blood on paper with 10 µL of 4% (w/v) sodium deoxycholate dried. Mechanically lysed blood and blood on SDOC-treated paper show similar errors at all hemoglobin concentrations, while whole blood shows increased error at higher hemoglobin concentrations Wavelength and Drying Time Optimization. In one set of experiments, absorption spectra from 300 nm to 800 nm of whole blood were obtained. The measured absorption spectra are depicted in FIG. 3, which depicts absorption spectra of 10 µL whole blood on Whatman 40 filter paper after 10 minutes of drying. Baseline correction was performed to normalize entire spectra so that minimum absorbances in the 650-800 nm region equate to zero. Absorbance values were taken by Cary 5000 UV-Vis-NIR spectrophotometer (Varian, Palo Alto, Calif.). As depicted in FIG. 3, optical densities were observed to drop below 0 above 600 nm, and spectra were corrected to adjust optical densities from 650 to 800 nm to 0. After baseline correction, optical densities at the various time points were qualitatively determined to be equivalent at local maxima of 545 and 577 nm and above 600 nm. Similarly, FIG. 4 depicts the measured (unadjusted) absorption spectrum of blood on SDOC-treated filter paper.

Figure 5B:
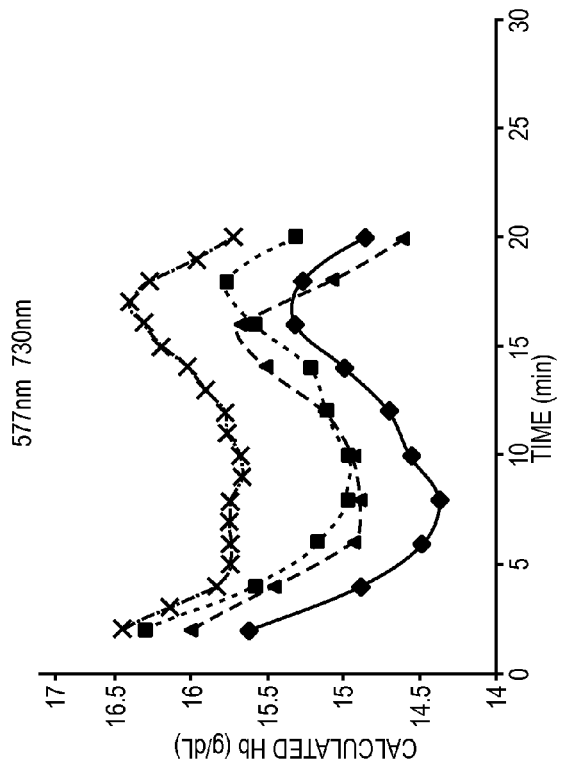
FIG. 5B depicts the absorbance difference between 577 nm and 730 nm over time, in accordance with aspects of the present disclosure.
Figure 5A:
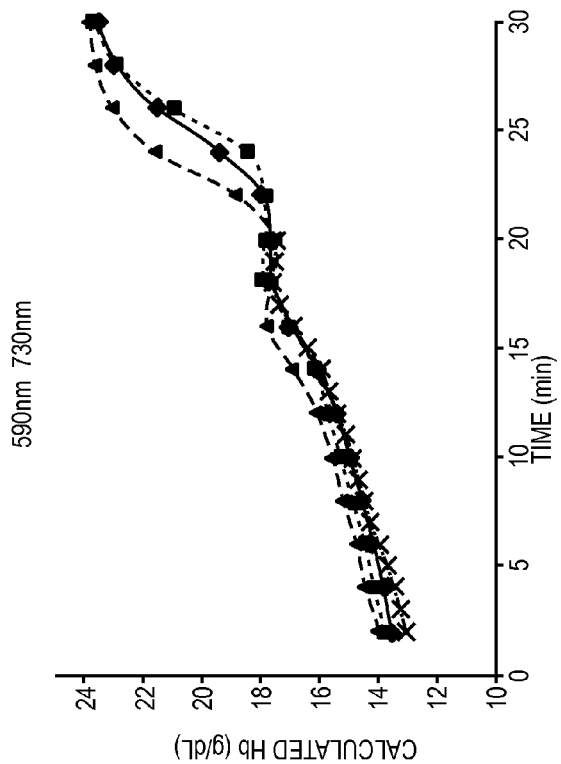
FIG. 5A depicts the absorbance difference between 590 nm and 730 nm over time, in accordance with aspects of the present disclosure.

In another set of experiments, absorption spectra from 350 nm to 800 nm of whole blood on SDOC-treated paper over the course of 30 minutes were measured for four samples of the same blood (FIGS. 5A and 5B). The difference between various pairs of wavelengths were examined for their absorbance characteristics over time; one wavelength was chosen on the hemoglobin spectrum (approximately 350 nm to 600 nm, see FIG. 4) and one on the flat or baseline region (≥600 nm). An isosbestic point for oxyhemoglobin and deoxyhemoglobin (590 nm, where the absorbance for both species is equal) gave the results most stable over time and most repeatable (FIG. 5A). Other wavelengths, e.g. 577 nm, gave less repeatable and less stable absorbance readings. The choice of "baseline" wavelength appeared to have little effect on the results. For the remainder of the tests, spectra were taken at 2 minutes for efficiency and consistency, and the absorbance difference between 590 nm and 730 nm was used to correlate with hemoglobin concentration.

Figure 6:
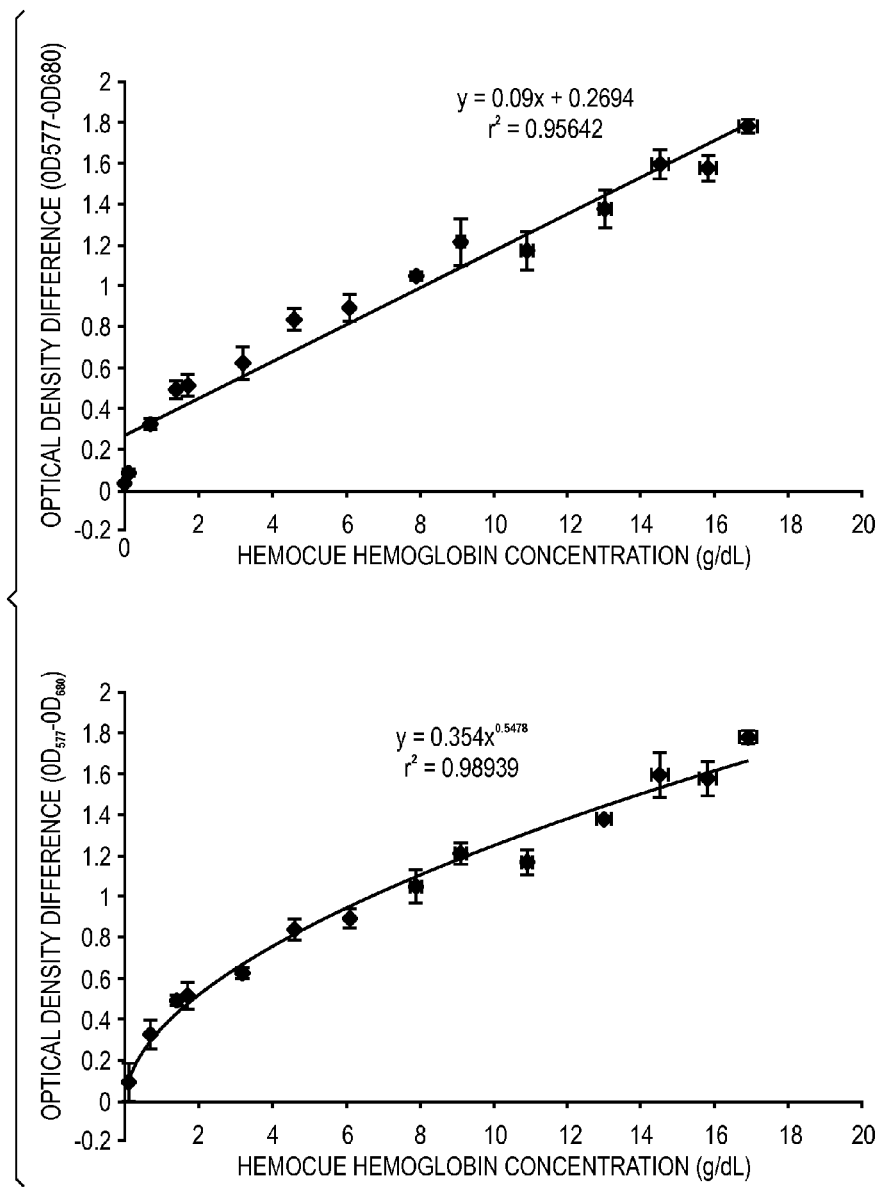
FIG. 6 depicts the difference in optical density at 577 and 680 nm vs hemoglobin concentration, in accordance with aspects of the present disclosure.

Spectrophotometric Detection of Simulated Anemia on Paper Media. In an initial set of experiments, average differences (n=2) in optical densities at the points of 577 and 680 nm of various dilutions of blood after exactly 10 minutes of drying were correlated with corresponding HemoCue hemoglobin values, as depicted in FIG. 6. Differences between the local maxima at 577 nm and minima of 680 nm were taken to reduce baseline error. Coefficient of determination ($r^2$) value was determined to be 0.989 for the power fit and 0.956 for the linear fit.

FIG. 6 depicts the difference in optical density at 577 and 680 nm vs hemoglobin concentration. Blood samples were obtained by diluting whole blood with purified plasma. Optical densities were taken by Cary 5000 UV-Vis-NIR spectrophotometer (Varian, Palo Alto, Calif.), and hemoglobin values were measured by HemoCue Hb 201+ (HemoCue, Ängelholm, Sweden). Plotted points are the differences between mean values of the optical densities at 577 and 680 nm for that dilution for two samples. Vertical error bars display the range of the standard deviation of the difference. Horizontal error bars display the ±1.5% error according to technical specifications of HemoCue. Best-fit power (bottom) and linear (top) regressions were found, and the resultant line, formula, and coefficient of determination ($r^2$) values are present on the graphs.

Figure 7:
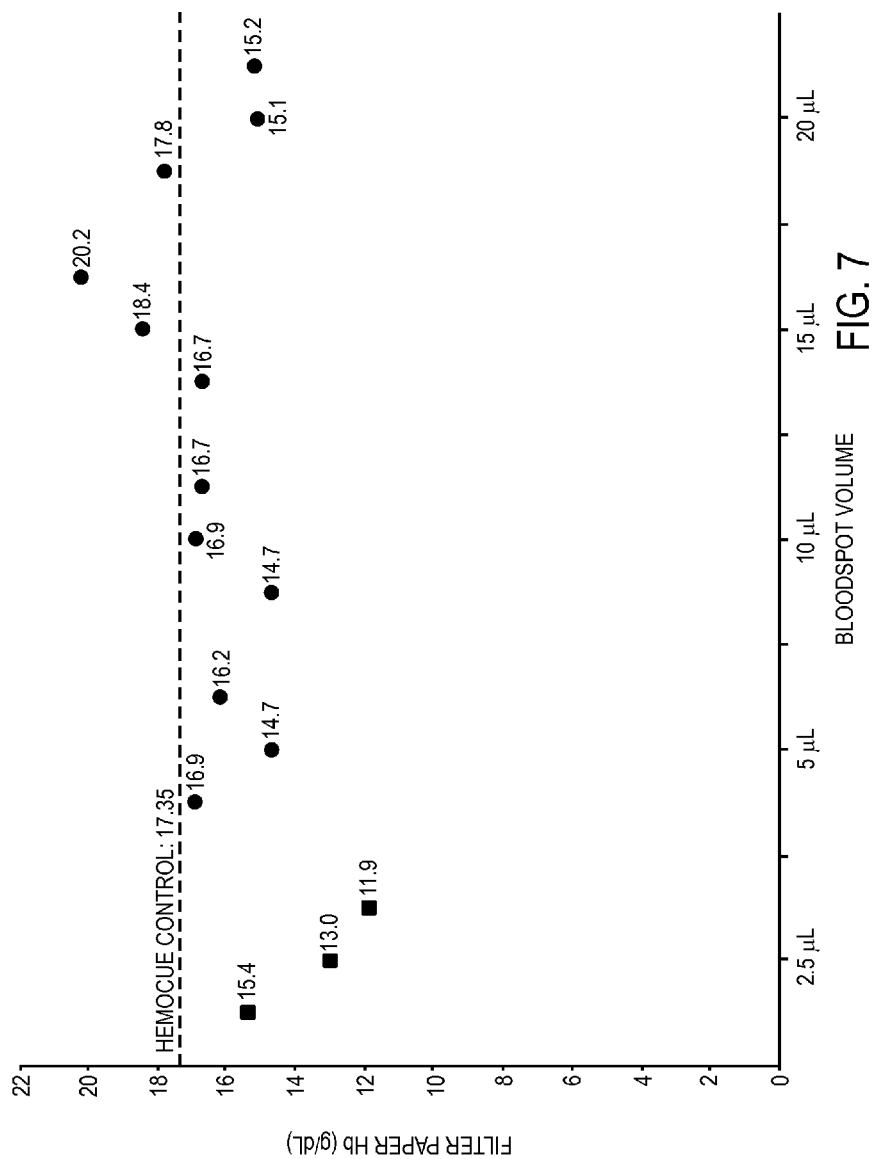
FIG. 7 depicts a comparison of calculated hemoglobin concentration of various blood spot volumes when compared against average, corresponding HemoCue® reading of 17.35 g/dL, in accordance with aspects of the present disclosure.

Volume Effects. In initial experiments, average differences (n=2) in optical densities at the points of 577 nm and 680 nm of various volumes of a whole blood sample and the linear and power relations were used to calculate hemoglobin values. These experimental hemoglobin values were compared to the hemoglobin value as measured by HemoCue®, and percent error was determined to range from less than 1% (10 μL and 15 μL) to 46.60% (5 μL) when using the linear relation and 8.7% (5 μL) to 54.54% (2.5 μL) when using the power relation. FIG. 7 depicts a comparison of calculated hemoglobin concentration from established relations from FIG. 6 when compared against average, corresponding HemoCue® reading of 17.35 g/dL.

Figure 8:
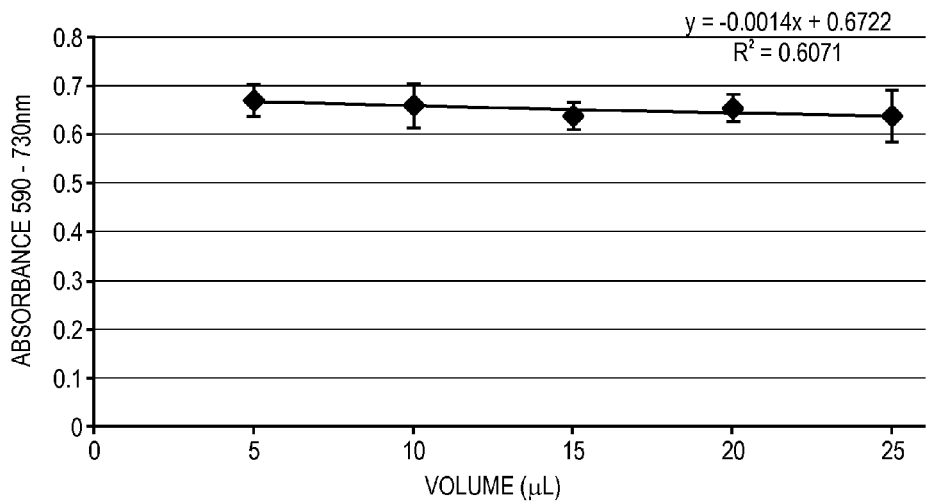
FIG. 8 depicts the absorbance difference of various volumes of blood on sodium deoxycholate-treated paper, in accordance with aspects of the present disclosure.

In other experiments, the absorbance difference between 590 nm and 730 nm was examined for various volumes of blood from one blood sample applied on SDOC-treated paper (FIG. 8). The absorbance difference is relatively constant for all volumes tested (5 μL to 25 μL), so this range would appear to be appropriate for measurements. In certain of these experiments, to help health workers gauge the appropriate volume for the blood spot, eight small dots were printed onto the paper in the shape of a circle which would roughly correspond to 10 μL of applied blood. The circle also denoted where the sodium deoxycholate lysing agent has been dried onto the paper.

Figure 9:
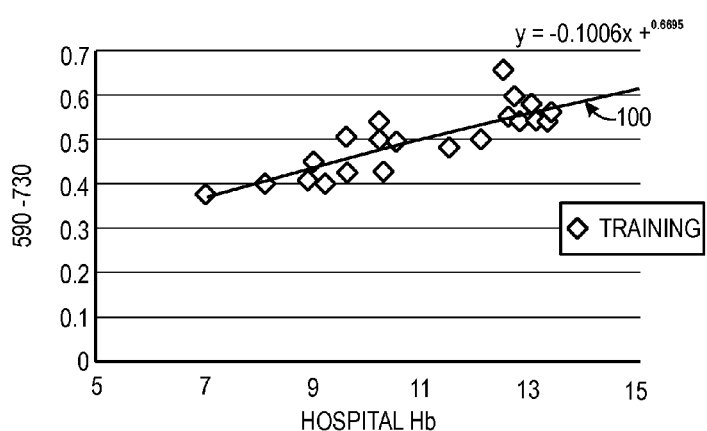
FIG. 9 depicts the best fit power line associated with a training set based on sample data, in accordance with aspects of the present disclosure.
Figure 10:
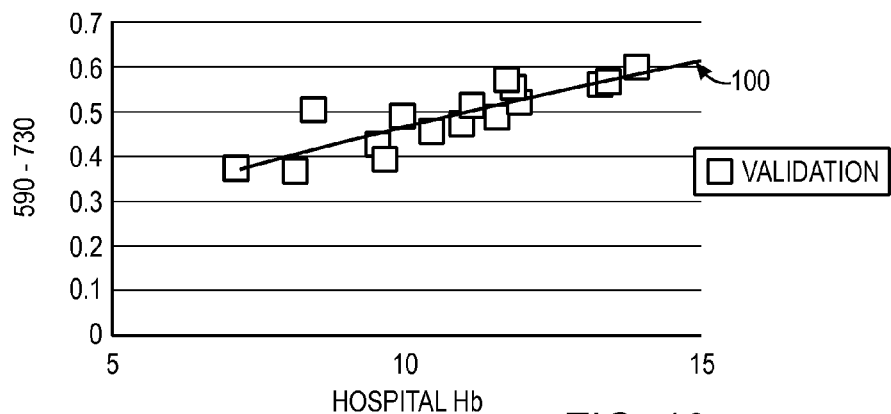
FIG. 10 depicts validation of the training data, in accordance with aspects of the present disclosure.
Figure 11:
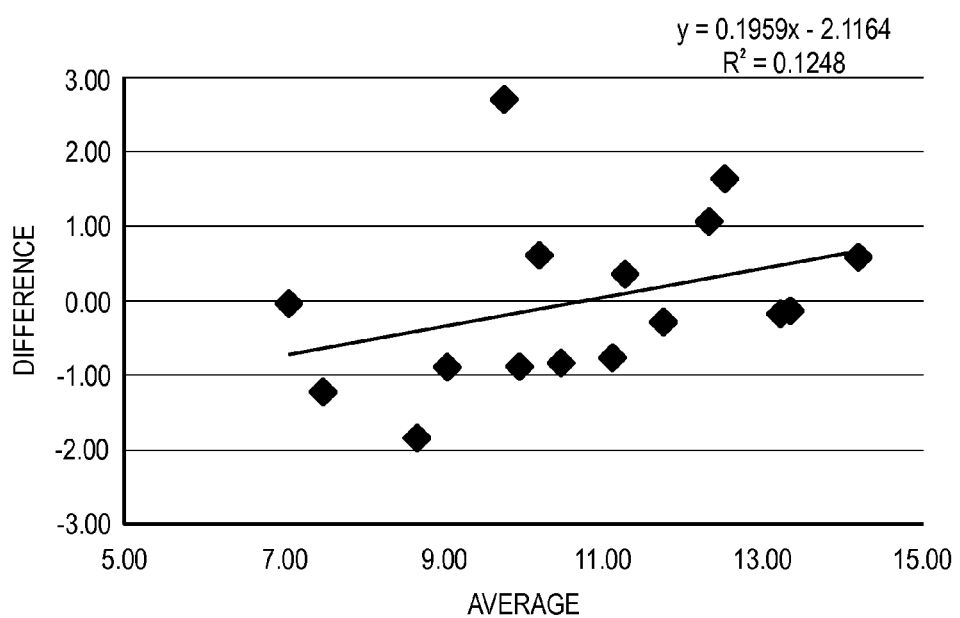
FIG. 11 depicts a Bland-Altman plot for the validation set comparing the calculated hemoglobin value to the HemoCue® reading, depicts the best fit power line associated with a training set based on sample data, in accordance with aspects of the present disclosure.

Turning to FIGS. 9-11, the results of training and validation of certain experiments are depicted. FIG. 9 depicts the best fit power line associated with a training set based on samples obtained from hospitalized patients applied to SDOC-treated paper. The results of validation of the training are depicted in FIG. 10. The validation was performed using samples obtained from hospitalized patients. The depicted line 100 represents the best fit line from training data for comparison. In FIG. 11, a Bland-Altman plot is depicted for the validation set comparing the average and difference of the hospital-determined hemoglobin concentration and the hemoglobin concentration calculated using the training line.

DISCUSSION. As discussed herein, a paper medium (e.g., filter paper or chromatography paper) can be an accurate and low-cost medium for spectrophotometric detection of blood hemoglobin concentration. In addition to the cost savings in using a paper-based approach to measuring hemoglobin, other considerations may favor such an approach. For example, the hard, plastic, and sharp nature of used cuvettes filled with blood necessitate considerations in minimizing biohazard risk. Filter paper alternative provides an advantage over the cuvette in the minimization of biohazard risk due to the filter paper's pliant nature. Furthermore, filter paper can be easily incinerated on-site to directly sterilize any potential contagions.

In addition, in certain embodiments it is anticipated that filter paper may be used as a low-cost medium for accurate spectrophotometric detection of blood hemoglobin concentration. For example a system may be employed that uses LED light emission at the target wavelengths, a photodiode to determine optical densities of blood on filter paper at these wavelengths, and a microcontroller to subtract optical densities at these wavelengths and correlate to an established correlation. Furthermore, effects of varying blood volume may be controlled by limiting spread on the filter paper by creating a 300° cut-out barrier below a pre-determined diameter and allowing for overflow of excess blood volume through connected filter paper 60° above the pre-determined diameter.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art, including combinations of aspects or features of the embodiments and examples disclosed herein. Such other examples are intended to be within the scope of the claims if they have structural elements that do not differ from the literal language of the claims, or if they include equivalent structural elements with insubstantial differences from the literal languages of the claims. The specific embodiments described above have been shown by way of example, and it should be understood that these embodiments may be susceptible to various modifications and alternative forms, including combinations of various features and aspects of the examples or embodiments discussed herein. It should be further understood that the claims are not intended to be limited to the particular forms disclosed, but rather to cover all modifications, equivalents, and alternatives falling within the spirit and scope of this disclosure.

The invention claimed is:

1. One or more non-transitory, machine readable media encoding routines that, when executed by a processor, cause acts to be performed comprising:

receiving a first input indicative of absorbance of light at a first wavelength through a blood sample on a paper medium;

receiving a second input indicative of absorbance of light at a second wavelength through the blood sample on the paper medium;

correcting for baseline intensity in the first input based on the second input to generate a normalized measure of absorbance by hemoglobin;

calculating a hemoglobin concentration using the normalized measure.

2. The one or more machine readable media of claim 1, wherein the hematocrit is calculated using an empirically determined correlation or constant relating optical density and hemoglobin concentration.

3. The one or more machine readable media of claim 1, wherein the first wavelength of light is about 590 nm.

4. The one or more machine readable media of claim 1, wherein the second wavelength of light is about 730 nm.

5. The one or more machine readable media of claim 1, wherein correcting for baseline intensity in the first input comprises subtracting the second input from the first input.

6. The one or more machine readable media of claim 1, wherein the first wavelength of light constitutes an isosbestic point for oxyhemoglobin and deoxyhemoglobin.

7. A method for measuring hemoglobin concentration, comprising the acts of:
- measuring the absorption of light by a blood sample on a paper medium at two wavelengths;
- subtracting a value representative of the absorption of light at the second wavelength from a value representative of the absorption of light at the first wavelength to derive a normalized absorption value; and
- calculating a hemoglobin concentration based on the normalized absorption value using an empirically determined correlation or constant relating optical density and hemoglobin concentration.

8. The method of claim 7, wherein the blood sample comprises lysed blood cells.

9. The method of claim 7, wherein the blood sample is lysed on the paper medium prior to the absorption of light being measured.

* * * * *